(12) United States Patent
Kawamura

(10) Patent No.: US 9,511,192 B2
(45) Date of Patent: Dec. 6, 2016

(54) MEDICAL SYRINGE

(71) Applicant: DAIKYO SEIKO, LTD., Tokyo (JP)

(72) Inventor: Hideaki Kawamura, Tokyo (JP)

(73) Assignee: DAIKYO SEIKO, LTD., Tokyo (JP)

( * ) Notice: Subject to any disclaimer, the term of this patent is extended or adjusted under 35 U.S.C. 154(b) by 0 days.

(21) Appl. No.: 14/142,135

(22) Filed: Dec. 27, 2013

(65) Prior Publication Data

US 2014/0188052 A1   Jul. 3, 2014

(30) Foreign Application Priority Data

Dec. 28, 2012  (JP) ................................ 2012-288551

(51) Int. Cl.
| | | |
|---|---|---|
| *A61M 5/00* | (2006.01) | |
| *A61M 5/315* | (2006.01) | |
| *A61M 5/31* | (2006.01) | |
| *A61M 5/50* | (2006.01) | |

(52) U.S. Cl.
CPC ......... *A61M 5/31505* (2013.01); *A61M 5/315* (2013.01); *A61M 5/3135* (2013.01); *A61M 5/31501* (2013.01); *A61M 2005/3101* (2013.01); *A61M 2005/5026* (2013.01)

(58) Field of Classification Search
CPC .................................................... A61M 5/315
USPC ................................................ 604/192–198
See application file for complete search history.

(56) References Cited

U.S. PATENT DOCUMENTS

| | | | | |
|---|---|---|---|---|
| 772,114 A | * | 10/1904 | Pappenheim | ................. 604/220 |
| 2,369,304 A | * | 2/1945 | Everett | ......................... 604/209 |
| 2,571,653 A | * | 10/1951 | Bastien | ......................... 604/198 |
| 3,747,812 A | * | 7/1973 | Karman et al. | ................ 222/387 |
| 3,890,971 A | * | 6/1975 | Leeson et al. | ................ 604/110 |
| 4,212,309 A | | 7/1980 | Moorehead | |
| 4,711,637 A | * | 12/1987 | Leigh et al. | ................... 604/220 |
| 4,731,068 A | | 3/1988 | Hesse | |
| 4,758,232 A | * | 7/1988 | Chak | ............................. 604/220 |
| 4,946,441 A | * | 8/1990 | Laderoute | ...................... 604/110 |
| 4,961,728 A | * | 10/1990 | Kosinski | ........................ 604/110 |
| 4,973,310 A | * | 11/1990 | Kosinski | ........................ 604/110 |

(Continued)

FOREIGN PATENT DOCUMENTS

| | | |
|---|---|---|
| EP | 0511402 | 11/1992 |
| JP | 05-115552 | 5/1993 |

(Continued)

OTHER PUBLICATIONS

Japanese Office Action issued in the corresponding Japanese Patent Application 2012-288551, dated Aug. 16, 2016.

*Primary Examiner* — Scott Medway

(74) *Attorney, Agent, or Firm* — Hamre, Schumann, Mueller & Larson, P.C.

(57) ABSTRACT

A medical syringe, having a syringe barrel, a piston, a plunger rod, and a plunger rod holder, wherein a barrel main body of the syringe barrel is formed to have a small inner diameter part and a large inner diameter part, the piston is formed such that the circular part is comprised of an elastic material and has an outer diameter larger than the inner diameter of the small inner diameter part of the barrel main body so that the outer periphery of the circular part can be brought into contact with the inner peripheral surface of the small inner diameter part by pressurizing, and the piston can be held in the large inner diameter part of the barrel main body in a state of being freely fitted thereto.

13 Claims, 9 Drawing Sheets

(56) References Cited

U.S. PATENT DOCUMENTS

| | | | |
|---|---|---|---|
| 5,106,372 A * | 4/1992 | Ranford | 604/110 |
| 5,108,378 A | 4/1992 | Firth et al. | |
| 5,112,315 A * | 5/1992 | Gloyer et al. | 604/195 |
| 5,215,524 A * | 6/1993 | Vallelunga et al. | 604/110 |
| 5,215,533 A * | 6/1993 | Robb | 604/195 |
| 5,215,536 A * | 6/1993 | Lampropoulos et al. | 604/220 |
| 5,263,934 A * | 11/1993 | Haak | 604/110 |
| 5,279,581 A | 1/1994 | Firth et al. | |
| 5,290,228 A | 3/1994 | Uemura et al. | |
| 5,312,365 A | 5/1994 | Firth et al. | |
| 5,441,486 A * | 8/1995 | Yoon | 604/167.03 |
| 5,514,107 A * | 5/1996 | Haber et al. | 604/197 |
| 5,607,399 A * | 3/1997 | Grimard et al. | 604/220 |
| 5,634,903 A * | 6/1997 | Kurose et al. | 604/110 |
| 5,700,247 A * | 12/1997 | Grimard et al. | 604/220 |
| 5,733,261 A * | 3/1998 | Obong | 604/110 |
| 5,803,918 A * | 9/1998 | Vetter et al. | 604/110 |
| 5,814,017 A * | 9/1998 | Kashmer | 604/110 |
| 5,817,065 A * | 10/1998 | Dufresne et al. | 604/199 |
| 5,891,104 A * | 4/1999 | Shonfeld et al. | 604/195 |
| 5,891,105 A * | 4/1999 | Mahurkar | 604/195 |
| 5,968,019 A * | 10/1999 | Lee | 604/195 |
| 5,997,511 A * | 12/1999 | Curie et al. | 604/195 |
| 6,030,366 A * | 2/2000 | Mitchell | 604/192 |
| 6,086,568 A * | 7/2000 | Caizza | 604/218 |
| 6,494,863 B1 * | 12/2002 | Shaw et al. | 604/110 |
| 6,986,756 B2 * | 1/2006 | Pelkey et al. | 604/110 |
| 6,991,618 B2 * | 1/2006 | Lau et al. | 604/110 |
| 7,004,929 B2 * | 2/2006 | McWethy et al. | 604/198 |
| 7,081,107 B2 * | 7/2006 | Kito et al. | 604/221 |
| 7,500,964 B2 * | 3/2009 | Shaw et al. | 604/197 |
| 7,544,180 B2 * | 6/2009 | Woehr | 604/110 |
| 7,842,017 B1 * | 11/2010 | Gray | 604/220 |
| 8,075,535 B2 | 12/2011 | Carrel et al. | |
| D660,418 S * | 5/2012 | Kuczek et al. | D24/130 |
| 8,372,044 B2 * | 2/2013 | Westbye et al. | 604/198 |
| 2003/0032928 A1 * | 2/2003 | Sudo et al. | 604/225 |
| 2005/0192544 A1 | 9/2005 | Wolbring et al. | |
| 2005/0240159 A1 * | 10/2005 | Kito et al. | 604/222 |
| 2010/0198165 A1 | 8/2010 | Zihlmann et al. | |
| 2012/0109072 A1 * | 5/2012 | Tabata et al. | 604/192 |
| 2012/0220952 A1 | 8/2012 | Zihlmann et al. | |
| 2013/0158486 A1 | 6/2013 | Zihlmann et al. | |
| 2013/0331798 A1 * | 12/2013 | Tachikawa et al. | 604/218 |

FOREIGN PATENT DOCUMENTS

| | | |
|---|---|---|
| JP | 02-220670 | 9/1999 |
| JP | 2006-528044 | 12/2006 |
| WO | WO 00/71185 | 11/2000 |
| WO | 2004105840 | 12/2004 |

* cited by examiner

MEDICAL SYRINGE

TECHNICAL FIELD

This invention relates to a medical syringe such as a filled-in use type syringe. In particular, this invention relates to a medical syringe that is capable of preventing an occurrence of creep deformation in a piston thereof.

BACKGROUND ART

As a medical syringe (hereinafter referred to as merely "syringe"), a pre-filled type syringe that is provided in a state that a medical solution is preliminarily filled in the syringe, a filled-in use type syringe that is provided in a state that a medical solution is not filled in the syringe, the medical solution being filled at the time of use, and the like are used.

With regard to the filled-in use type syringe as mentioned above, a method that parts such as a syringe barrel, a piston, a plunger rod are provided in a state separated from each other and are assembled at the time of use may be considered. However, the above-mentioned method not only increases a burden of nurses who are busy, but also raises a concern about hygiene issue such as a fear that the syringe is contaminated by microorganisms at the assembling work. Consequently, it is common that the filled-in use type syringe is provided as a pre-assembled type syringe in which parts such as a syringe barrel, a piston, a plunger rod are preliminarily assembled. The pre-assembled type syringe is included in a well-known, commonly used art, thus there is no prior art literature information to be described.

SUMMARY OF INVENTION

Technical Problem

However, in the case of the pre-assembled type syringe, the piston is loaded within the syringe barrel over a long period, thus there is a problem that stress occurs in the piston, so as to cause the piston to be creep-deformed. If the piston is creep-deformed, it is not preferable since the syringe decreases in sealing properties so as to cause a disadvantage such as a leak of the medical solution.

In addition, the filled-in use type syringe has a short contact time with the medical solution, different from the pre-assembled type syringe, and it has an actual using time of at longest a half-day. Therefore, in the filled-in use type syringe, there is a circumstance that reduction in the manufacturing cost is becoming more important than a long-term guarantee of chemical resistance and sealing properties. As the measurement of the reduction in manufacturing cost, a method that the piston is comprised of a thermoplastic material similarly to the plunger rod, and the piston is formed together with the plunger rod by a simultaneous molding may be considered, the piston conventionally being comprised of vulcanized rubber and needed to be manufactured by a process separated from the manufacturing process of the plunger rod.

As the method that the piston is formed together with the plunger rod by the simultaneous molding, a method configured such that a piston is comprised of urethane rubber, silicone rubber or thermoplastic rubber, and the piston is formed together with the plunger rod by an integral molding such as a two-color molding, and the like are proposed (for example, refer to JP-1996(Heisei 8)-280804 A1). However, commencing with the above-mentioned method, a case that a thermoplastic resin or a thermoplastic elastomer that is inferior to elasticity than vulcanized rubber is used as a material of the piston, it is expected that the problem of the creep deformation of the piston will further remarkably occur. Actually, a syringe including a piston comprised of the thermoplastic resin or thermoplastic elastomer is hardly put to practical use.

It is an object of the present invention to solve the above-mentioned problem and provide a medical syringe that is capable of preventing an occurrence of the creep deformation in the piston, even if the piston is loaded within the syringe barrel over a long period as the pre-assembled type syringe, furthermore is capable of preventing an occurrence of disadvantages such as decrease in sealing properties of the syringe, a leak of the medical solution from the syringe.

Solution to Problem

The inventors et al. have earnestly investigated the above-mentioned problems, as a result, it has been convinced that the above-mentioned problems can be solved and the object can be achieved by configuring a medical syringe such that a barrel main body of syringe barrel is formed to have a small inner diameter part in which a medical solution is filled on the tip side thereof, and have a large inner diameter part that has a larger inner diameter than the small inner diameter part on the end side thereof, and a piston is held in the large inner diameter part in a state before use, thus the present invention has been completed. Namely, according to the present invention, a medical syringe as shown below can be provided.

In accordance with the present invention, a medical syringe is provided, the medical syringe comprising a syringe barrel having a barrel main body formed in a substantially cylindrical shape, a nozzle formed at the tip of the barrel main body and a flange formed at the end of the barrel main body, a piston having a circular part which has an outer diameter that can be inserted into an interior space of the barrel main body and a plunger rod formed at the end of the piston in a protruding manner in the shape of a rod having a diameter smaller than the outer diameter of the circular part of the piston, and a plunger rod holder having a rod insertion part into which the plunger rod can be inserted, wherein the barrel main body is formed to have a small inner diameter part on the tip side thereof, and have a large inner diameter part that has a larger inner diameter than the small inner diameter part on the end side thereof, the piston is formed such that the circular part thereof is comprised of an elastic material and has an outer diameter larger than the inner diameter of the small inner diameter part of the barrel main body so that the outer periphery of the circular part can be brought into contact with the inner peripheral surface of the small inner diameter part by pressurizing, and the circular part thereof has an outer diameter equal to or smaller than the inner diameter of the larger inner diameter part of the barrel main body, the plunger rod holder is mounted on the end of the barrel main body so that the rod insertion part is located at the center of the barrel main body, the plunger rod is held at the center of the barrel main body in a state of being inserted into the rod insertion part of the plunger rod holder, and the piston can be held in the large inner diameter part of the barrel main body in a state of being freely fitted thereto.

It is preferable that the piston comprises a shaft portion and a brim portion as the circular part formed in the outer peripheral side of the shaft portion, and the brim portion is comprised of a resin.

It is preferable that the plunger rod has a recessed groove formed to temporarily fix the plunger rod in a state of the piston being located in the large inner diameter part of the barrel main body, the recessed groove is formed by reducing the outer diameter of the plunger rod than those of the other parts, the recessed groove is formed at a position that the length from the recessed groove to the tip of the piston is shorter than the length of the large inner diameter part of the barrel main body, and when the recessed groove is engaged with an inner edge portion of the rod insertion part in the plunger rod holder, the piston is located in the large inner diameter part of the barrel main body.

It is preferable that the plunger rod has a recessed groove configured to temporarily fix the plunger rod in a state that the piston is located in the large inner diameter part of the barrel main body, the recessed groove is formed by disposing a pair of front and rear projecting portions in the outer periphery side of the plunger rod so as to enlarge the outer diameter of the plunger rod than those of the other parts, the recessed groove is formed at a position that the length from the recessed groove to the tip of the piston is shorter than the length of the large inner diameter part of the barrel main body, and when the recessed groove is engaged with an inner edge portion of the rod insertion part in the plunger rod holder, the piston is located in the large inner diameter part of the barrel main body.

It is preferable that the engagement structure of the recessed groove and the inner edge portion is configured to permit only the movement in the insertion direction of the plunger rod and to inhibit the movement in the extraction direction of the plunger rod.

It is preferable that the rod insertion part of the plunger rod holder comprises a plurality of flexible boards formed in a protruding manner in the inner edge portion side of the plunger rod holder in a state of being slightly inclined in the insertion direction of the plunger rod, and the rod insertion part of the plunger rod holder comprises a plurality of flexible pins formed in a protruding manner in the inner edge portion side of the plunger rod holder in a state of being slightly inclined in the insertion direction of the plunger rod.

It is preferable that the plunger rod has a step part formed so as not to allow the piston inserted into the small inner diameter part of the barrel main body to move backward to the large inner diameter part of the barrel main body, wherein the step part is formed by reducing the outer diameter of the end side of the plunger rod than that of the tip side thereof, the step part is formed at a position that the length from the step part to the tip of the piston is longer than the length of the large inner diameter part of the barrel main body, and when the step part is engaged with the inner edge portion of the rod insertion part in the plunger rod holder, the piston is located in the small inner diameter part of the barrel main body.

It is preferable that the barrel main body is configured such that the large inner diameter part has a plurality of ribs projecting toward the center side of the barrel main body and extending in the axis direction of the syringe barrel, and the piston can be held in the plural ribs in a state of being freely fitted thereto.

It is preferable that the piston is comprised of a thermoplastic elastomer or a thermoplastic resin.

Advantageous Effects of Invention

The medical syringe according to the present invention is capable of preventing an occurrence of the creep deformation in the piston, even if the piston is loaded inside of the syringe barrel over a long period as the pre-assembled type syringe, furthermore is capable of preventing an occurrence of disadvantages such as decrease in sealing properties of the syringe, leak of medical solution from the syringe.

BRIEF DESCRIPTION OF DRAWINGS

The preferred embodiments according to the invention will be explained below referring to the drawings, wherein:

FIG. 4-1 is a partially cutaway side view schematically showing a partially enlarged piston of the medical syringe shown in FIG. 1;

FIG. 4-2 is a partially cutaway side view schematically showing a partially enlarged piston of the medical syringe according to another embodiment of the present invention;

FIG. 4-3 is a partially cutaway side view schematically showing a partially enlarged piston of the medical syringe according to the other embodiment of the present invention;

FIG. 7-1 is a conceptual view schematically showing a positional relationship between the respective components of the medical syringe shown in FIG. 1 in a state before use;

FIG. 7-2 is a conceptual view schematically showing a positional relationship between the respective components of the medical syringe shown in FIG. 1 in a state of use; and FIG. 7-3 is a conceptual view schematically showing a positional relationship between the respective components in a state of the plunger rod of the medical syringe shown in FIG. 1 being pulled out at a maximum.

DESCRIPTION OF EMBODIMENTS

Figure 1:
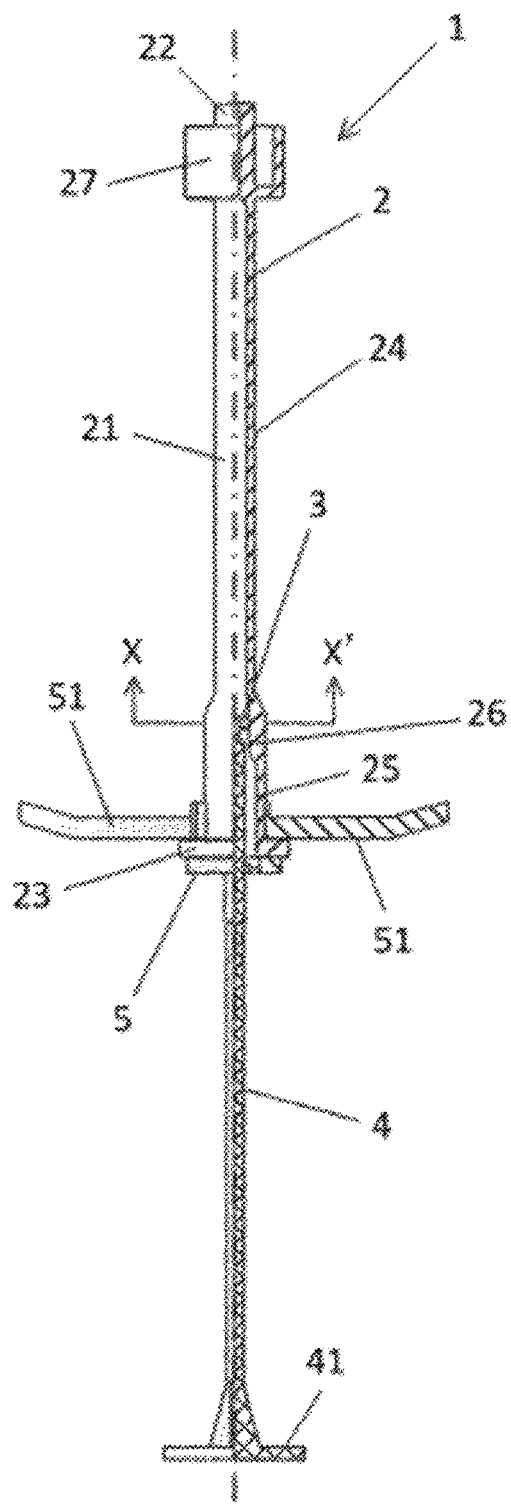
FIG. 1 is a partially cutaway side view schematically showing a medical syringe according to one embodiment of the present invention when viewed from the direction perpendicular to the center axis thereof.

The preferred embodiments according to the present invention will be explained below referring to the drawings. In the following embodiments, the same reference numerals as the first embodiment are used for indicating elements having the same structure and function as the first embodiment, and the explanation thereof may be omitted.

[1] Medical Syringe

The present invention relates to a medical syringe. FIG. 1 is a partially cutaway side view schematically showing a medical syringe according to one embodiment of the present invention when viewed from the direction perpendicular to the center axis thereof. The right side of the figure shows a cross-section surface cut along the center axis of the medical syringe. The medical syringe according to the present invention at least includes a syringe barrel 2, a piston 3, a plunger rod 4, and a plunger rod holder as the medical syringe 1 shown in FIG. 1.

[1-1] Syringe Barrel

As shown in FIG. 1, the medical syringe according to the present invention includes the syringe barrel 2 having a barrel main body 21 formed in a substantially cylindrical shape, a nozzle 22 formed at the tip of the barrel main body 21 and a flange 23 formed at the end of the barrel main body 21.

[1-1A] Barrel Main Body

As shown in FIG. 1, in the medical syringe according to the present invention, the barrel main body 21 is formed in a substantially cylindrical shape, in particular, is formed to have a small inner diameter part 24 having a small inner diameter on the tip side thereof, and have a large inner diameter part 25 that has a larger inner diameter than the small inner diameter part 24 on the end side thereof. The barrel main body 21 is formed in the above-mentioned shape, thereby the piston is capable of being held in a state of being freely fitted to the large inner diameter part of the barrel main body. The inner diameter of the small inner diameter part and the large inner diameter part is not particularly limited to specific value. However, it is preferable that the inner diameter of the small inner diameter part falls within the range of 1.5 to 3.5 mm and the inner diameter of the large inner diameter part falls within the range of 1.6 to 7.0 mm.

As shown in FIG. 1, in the medical syringe according to the present invention, it is preferable that the barrel main body 21 is formed in a cylindrical shape having different diameters such that the large inner diameter part 25 has an outer diameter larger than the small inner diameter part 24. The above-mentioned shape has an advantage that the outer diameter of the large inner diameter part 25 is large, thus the medical syringe is easily held so that operability thereof can be enhanced. In addition, in the medical syringe according to the present invention, a medical solution is filled in only the small inner diameter part 24 and is not filled in the large inner diameter part 25. Consequently, the large inner diameter part is held at the operation, thereby heat of fingers is hard to conduct to the medical solution, thus the medical solution can be prevented from an increase in temperature.

However, it is not necessary for the barrel main body to have a cylindrical shape having different diameters as the barrel main body 21 shown in FIG. 1, as long as the barrel main body is configured such that the small inner diameter part and the large inner diameter part are different in the inner diameter from each other. For example, the barrel main body can be also configured such that the small inner diameter part and the large inner diameter part have the same outer diameter, and are different in only the inner diameter from each other (not shown). Namely, the small inner diameter part and the large inner diameter part can be formed due to only the change of the wall thickness of the barrel main body. The barrel main body having the above-mentioned structure has an outer shape in which a step part is not formed, different from the barrel main body 21 of a cylindrical shape having different diameter shown in FIG. 1. Consequently, moldability of the syringe barrel and thus production yield of the mold product are enhanced so that the usage of the resin which is a raw material of the syringe barrel can be saved.

As shown in FIG. 1, in the medical syringe according to the present invention, it is preferable that the barrel main body 21 is configured such that the small inner diameter part 24 and the large inner diameter part 25 are continuously connected to each other via a sloping surface having a gentle angle that is not more than 60 degrees. If the barrel main body is configured such that the small inner diameter part and the large inner diameter part have the same outer diameter and are different in only the inner diameter from each other, the barrel main body can be also configured such that only the inner peripheries of the small inner diameter part and the large inner diameter part are continuously connected to each other via a sloping surface.

As explained above, the "substantially cylindrical shape" mentioned in the present invention includes a cylindrical shape having different diameter, a shape that the small inner diameter part and the large inner diameter part have the same outer diameter, and are different in only the inner diameter from each other, and a shape that the small inner diameter part and the large inner diameter part are continuously connected to each other via a sloping surface. Namely, the terms "substantially cylindrical shape" include a shape that a plurality of cylindrical parts having different inner and/or outer diameter respectively are assembled with each other.

As shown in FIG. 1, the medical syringe according to the present invention is configured such that the piston 3 is capable of being held in a state of being freely fitted to the large inner diameter part 25 of the barrel main body 21. In a state before use, the piston 3 is held in the large inner diameter part 25 instead of the small inner diameter part 24 in which the medical solution is filled, thereby the piston 3 is not pushed by pressurizing to the inner periphery of the barrel main body 21 so that the occurrence of stress in the piston 3 can be prevented. This makes it possible to effectively prevent the occurrence of creep deformation in the piston 3.

The terms "state of being freely fitted" mentioned in the present invention mean a state that the piston is fitted to the large inner diameter part without occurrence of stress therein (namely without being pushed by pressurizing to the inner periphery of the large inner diameter part) regardless of whether the outer periphery of the piston (particularly the outer periphery of the circular part) is brought into contact with the inner periphery of the large inner diameter part of the barrel main body or not. More particularly, the terms mean not only a state that there is an air space between the outer periphery of the piston and the inner periphery of the large inner diameter part, thus the outer periphery and the inner periphery are perfectly contactless with each other, but also a state that all or part of the outer periphery of the piston is lightly brought into contact with the inner periphery of the large inner diameter part, but the outer periphery is not pushed by pressurizing to the inner periphery, thus stress does not occur in the piston.

As shown in FIG. 1, it is preferable that the medical syringe according to the present invention is configured such that a plurality of ribs 26 projecting toward the center side of the barrel main body 21 and extending in the axis direction of the syringe barrel 2 are formed in the large inner diameter part 25 of the barrel main body 21, and the piston 3 can be held in the plural ribs 26 in a state of being freely fitted thereto.

Figure 3:
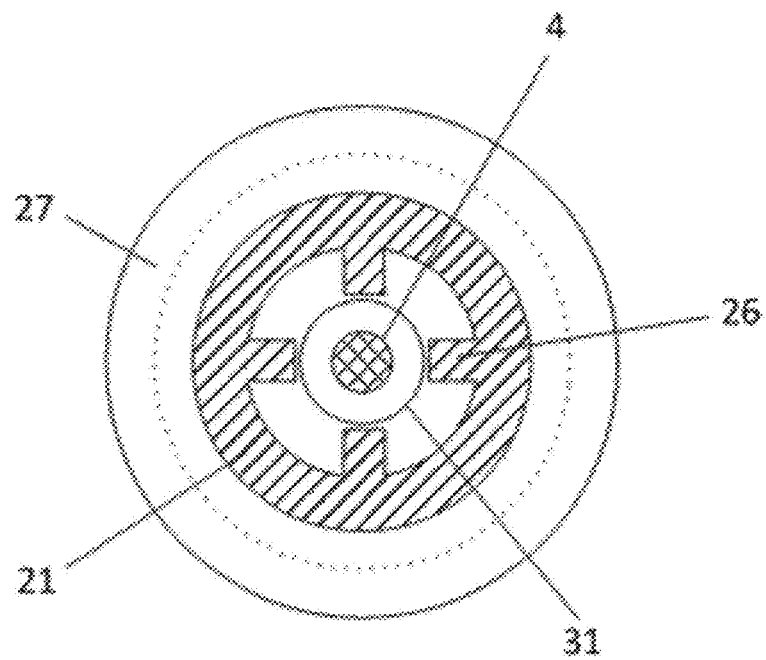
FIG. 3 is a cross-sectional view taken along the line X-X' in FIG. 1.

FIG. 3 is a cross-sectional view taken along the line X-X' in FIG. 1. As shown in FIG. 3, the medical syringe 1 is configured such that the brim portion 31 that constitutes a part of the outer periphery of the piston 3 and the rib 26 that constitutes a part of the inner periphery of the large inner diameter part 25 are maintained in a non-contact state. As shown in FIG. 3, the rib 26 is not brought into contact with the brim portion 31, but projects to the location extremely close to the brim portion 31, thus it has a guiding function of the piston 3. Namely, if the plunger rod 4 is inclined relative to the center axis direction of the syringe barrel 2, the piston 3 is brought into contact with the rib 26, thus the piston 3 can be pushed into the syringe barrel 2 along the center axis of the syringe barrel 2.

The medical syringe shown in FIG. 3 is configured such that four ribs 26 are formed, the ribs 26 extending along the center axis direction of the syringe barrel 2. In addition, the four ribs 26 are arranged at 90 degrees intervals in the center angle around the center axis of the syringe barrel. However, the number of the ribs is not limited to four. In consideration of exerting the guiding function of the piston, and not excessively complicating the structure of the syringe barrel, it is preferable that three to six ribs are formed and these ribs are arranged at equal intervals. The height of the rib is not particularly limited, but it is preferable that the height falls within the range of 0.5 to 2.5 mm.

Figure 2:
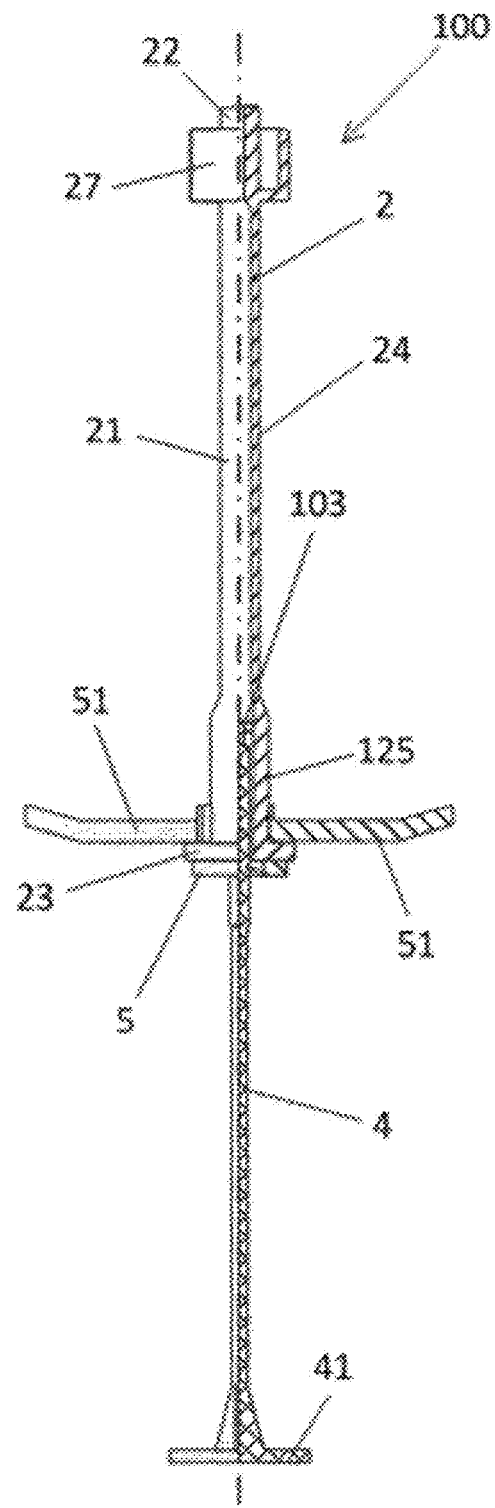
FIG. 2 is a partially cutaway side view schematically showing a medical syringe according to another embodiment of the present invention when viewed from the direction perpendicular to the center axis thereof.

FIG. 2 is a partially cutaway side view schematically showing a medical syringe according to another embodiment of the present invention when viewed from the direction perpendicular to the center axis thereof. Similarly to FIG. 1, the right side of the figure shows a cross-section surface cut along the center axis of the medical syringe. It is not indispensable that the medical syringe according to the present invention is configured such that the ribs are formed in the large inner diameter part as the embodiment shown in FIG. 1. For example, as the medical syringe 100 shown in FIG. 2, it can be also configured such that the piston 3 can be held in a state of being freely fitted by the inner periphery of the large inner diameter part 125 without forming the ribs in the large inner diameter part 125. Namely, the medical syringe 100 shown in FIG. 2 is configured such that the large inner diameter part 125 is formed to have an inner diameter smaller than the large inner diameter part 25 of the medical syringe 1 shown in FIG. 1, and the ribs are not formed. The structure in which the ribs are not formed is preferable in terms of being able to simplify the structure of the syringe barrel.

[1-1B] Nozzle

As shown in FIG. 1, the medical syringe according to the present invention is configured such that the barrel main body 21 has a nozzle 22 formed at the tip thereof. In the nozzle 22, an inner hole that passes through the nozzle 22 along the center axis of the nozzle 22 is formed. Via the inner hole, the interior space and the exterior space of the barrel main body 21 are communicated with each other.

As the nozzle, for example, a nozzle that has a structure based on ISO standards can be used. The medical syringe 1 shown in FIG. 1 is configured such that a Luer lock 27 for preventing an injection needle or the like from dropping out is attached to the nozzle 22. However, it is not indispensable that the Luer lock is attached to the medical syringe according to the present invention.

[1-1C] Flange

Figure 6:
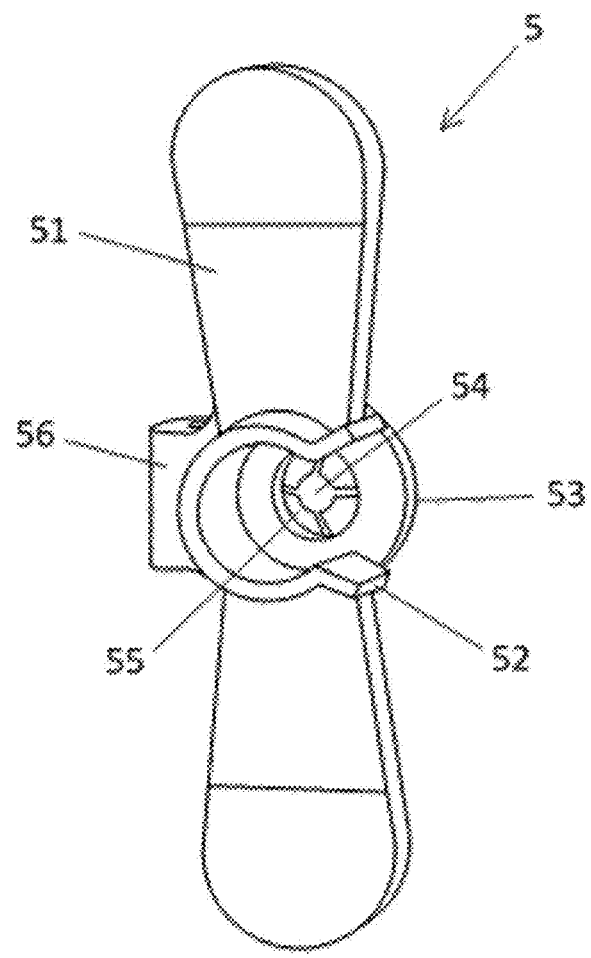
FIG. 6 is a perspective view schematically showing a plunger rod holder of the medical syringe shown in FIG. 1.

As shown in FIG. 1, the medical syringe according to the present invention is configured such that the barrel main body 21 has a flange 23 formed at the end thereof. Normally, the flange is formed in a circular ring shape that has an outer diameter of approximately 1.5 to 3 times the outer diameter of the barrel main body 21 (the large inner diameter part 25) as the flange 23 shown in FIG. 1. However, in the medical syringe according to the present invention, the shape of the flange is not limited to the circular ring shape. For example, a flange that has a two-blade shape projecting from only the parts located at the right and left of the outer periphery of the barrel main body, not from the whole outer periphery thereof, can be also used (not shown). In case of the flange having the two-blade shape, in order to enhance operability of the medical syringe, it is preferable that the projecting length is set to a length that the flange can be caught by adult fingers, particularly is set such that the one side length is about 2 cm (at least not less than 1.5 cm). As shown in FIG. 6, the medical syringe 1 shown in FIG. 1 is configured such that the plunger rod holder 5 has a finger catching part 51 having the two-blade shape. However, as shown above, if the flange of the syringe barrel is configured to have the two-blade shape, it is not necessary for the plunger rod holder to have the finger catching part.

[1-1D] Materials

The syringe barrel (the barrel main body, nozzle, flange) can be formed, for example, by an integral molding that uses a resin. It is preferable that the resin is a thermoplastic hard resin that is excellent in mechanical strength and is capable of producing molding products in large volume at low cost. For example, a polycycloolefin (PCO) based resin, a polyethylene (PE) based resin, a polypropylene (PP) based resin, a polycarbonate (PC) based resin, a polyvinylchloride (PVC) based resin, and the like can be used. Of these resins, the PCO based resin is preferable and a cycloolefin polymer (COP) is more preferable, the resin and polymer having a low eluting property and being excellent in transparency and gas barrier property. Further, in the present specification, the "polyX based resin" and "polyX based elastomer" mean a resin and an elastomer that include a homopolymer of X and a copolymer of X. For example, the PCO based resin includes the COP and a cycloolefincopolymer (COC).

[1-2] Piston

As shown in FIG. 1, the medical syringe according to the present invention includes the piston 3 having a circular part which has an outer diameter to be capable of being inserted into an interior space of the barrel main body. The circular part of the piston 3 is brought into contact with the inner peripheral surface of the small inner diameter part 24 of the barrel main body 21 by pressurizing, thereby the medical syringe 1 is capable of exerting sealing properties. The "circular" of "the circular part" means that a shape viewed from the direction perpendicular to the axis of the piston is circular. Consequently, in case that the piston is formed in a columnar shape or a cylindrical shape on the whole, parts having these shapes constitute the circular part. In addition, if the piston has a discoid shape or a circular ring shape, parts having these shapes constitute the circular part.

In the medical syringe according to the present invention, the circular part of the piston is comprised of an elastic material. As the elastic material, a vulcanized rubber, a thermoplastic elastomer, a thermoplastic resin and the like can be used. However, the present invention can be preferably used for a medical syringe configured such that the piston is comprised of the thermoplastic elastomer, or the thermoplastic resin, particularly is comprised of the thermoplastic resin. These materials are easily creep-deformed in comparison with the vulcanized rubber, thus the effect of the present invention can be exerted at a maximum.

As the thermoplastic elastomer, for example, a polystyrene based elastomer, an ethylene-propylene based elastomer, a polyisobutylene based elastomer, and the like can be used. As the thermoplastic resin, for example, a PE based resin, a PP based resin, a PC based resin, an ABS based resin, a polyamide based resin, a polyester based resin, and the like can be used. Of these resins, it is preferable that the piston is comprised of the PE based resin, the PP based resin, or the PC based resin, the resins being cheap in price and excellent in strength and hardness. The thermoplastic elastomer and the thermoplastic resin can be used individually or in mixture of not less than two thereof.

As shown in FIG. 1, in the medical syringe according to the present invention, the piston 3 is configured such that the circular part thereof has the outer diameter larger than the inner diameter of the small inner diameter part 24 of the barrel main body 21 so that the outer periphery of the circular part is capable of being brought into contact with the inner peripheral surface of the small inner diameter part 24 by pressurizing, and the circular part thereof has the outer diameter equal to or smaller than the inner diameter of the larger inner diameter part 25 of the barrel main body 21. The piston is formed in the above-mentioned shape, thereby in a state before use, the piston is arranged in the larger inner diameter part of the barrel main body, so that the occurrence of creep-deformation in the piston can be prevented, and in a state in use, the piston is moved to the small inner diameter part of the barrel main body and the piston is allowed to slide on the inner peripheral surface in a condition of being brought into contact with the inner peripheral surface, so that the original function (suction and injection of medical solution) as a piston can be exerted. Concrete value of the outer diameter of the circular part is not particularly limited, but it is preferable that the value falls within the range of 1.6 to 4.0 mm.

Figures 1, 4:
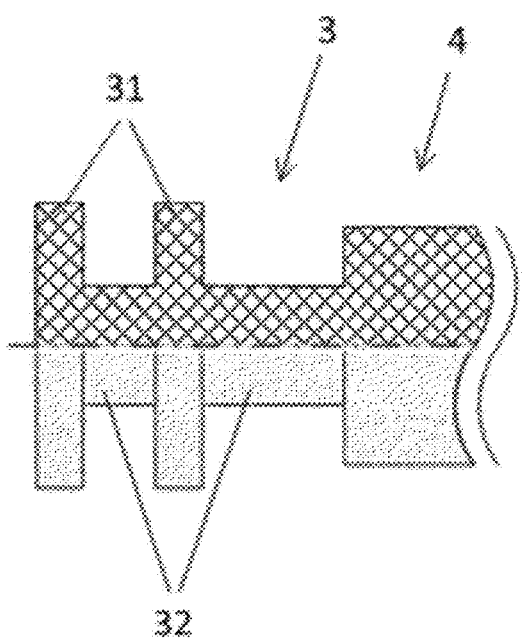
Figures 2, 4:
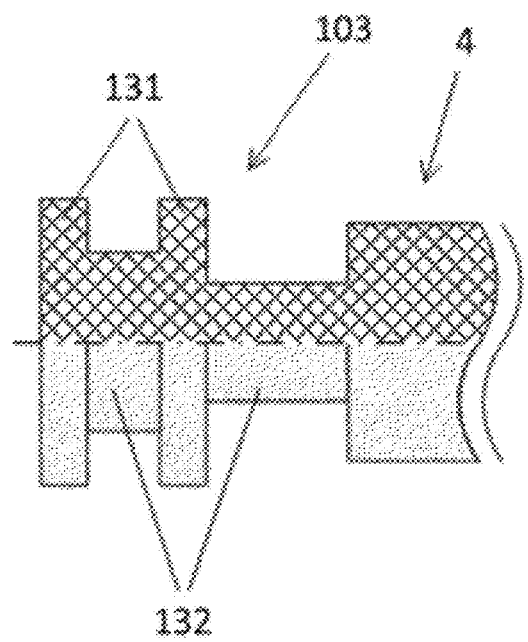
Figures 3, 4:
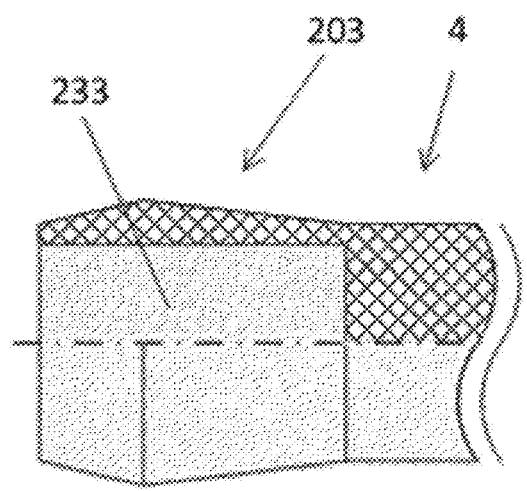

FIG. 4-1 is a partially cutaway side view schematically showing a partially enlarged piston of the medical syringe shown in FIG. 1. The upper part of FIG. 4-1 shows a cross-section surface when the piston is cut along the center axis thereof. As shown in FIG. 4-1, in the medical syringe according to the present invention, it is preferable that the piston 3 includes a shaft portion 32 and a brim portion 31 formed in the outer peripheral side of the shaft portion 32, and the brim portion 31 is comprised of a resin, has an outer diameter larger than the inner diameter of the small inner diameter part of the barrel main body so as to be brought into contact with the inner peripheral surface of the small inner diameter part by pressurizing, and has an outer diameter equal to or smaller than the inner diameter of the larger inner diameter part of the barrel main body.

The piston 3 shown in FIG. 4-1 is formed in a shape that two brim portions 31 are mounted on the outer periphery of the shaft portion 32. Namely, in the piston 3, the brim portion 31 having the circular ring shape constitutes the circular part. The piston has the above-mentioned structure, thereby even if the piston is comprised a hard resin, flexibility can be provided, and sealing properties and slidability required for the piston can be provided. Consequently, the plunger rod (the Rockwell hardness: about R70 to 120) needed to have hardness and the piston can be formed together by an integral molding using the same material, so that the medical syringe can be simplified in structure and can be reduced in the manufacturing cost. In the piston 3 shown in FIG. 4-1, the two brim portions 31 are respectively located at the tip of the shaft portion 32 and at the place slightly nearer the tip than the midpoint of the shaft portion 32 in the longitudinal direction.

FIG. 4-2 is a partially cutaway side view schematically showing a partially enlarged piston of the medical syringe according to another embodiment of the present invention. In FIG. 4-2, similarly to FIG. 4-1, the upper part of FIG. 4-2 shows a cross-section surface when the piston is cut along the center axis thereof. In a piston 103, two brim portions 131 having a circular ring shape constitute the circular part. The piston 103 shown in FIG. 4-2 is configured such that a part of the shaft portion 132 sandwiched between the two brim portions 131 is formed to have an outer diameter larger than another part thereof. Due to the above-mentioned structure, the brim portions 131 are reduced in a flexible area thereof, thus the two brim portions 131 are hard to be flexed in comparison with the piston 3 shown in FIG. 4-1. Consequently, although the brim portions 131 are reduced in slidability, those can provide an advantage that the medical syringe is improved in sealing properties.

FIG. 4-3 is a partially cutaway side view schematically showing a partially enlarged piston of the medical syringe according to the other embodiment of the present invention. In FIG. 4-3, similarly to FIG. 4-1, the upper part of FIG. 4-3 shows a cross-section surface when the piston is cut along the center axis thereof. A piston 203 shown in FIG. 4-3 is configured to have a part in which the outer diameter is maximized, at the place slightly nearer the tip than the midpoint in the longitudinal direction, and to be formed in a substantially barrel-like shape that the outer diameter is gradually decreased from the above-mentioned part to the tip and the end. In the piston having the above-mentioned structure, the maximum part of the outer diameter is brought into contact with and slides on the inner periphery of the small inner diameter part. Namely, in the piston 203 shown in FIG. 4-3, the maximum part of the outer diameter constitutes the circular part. In the above-mentioned structure, a hollow space 233 is formed within the piston 203 having a substantially barrel-like shape, and due to the hollow space 233, shape-followability and flexibility are provided for the piston 203.

The piston 203 having a substantially barrel-like shape is hard to be molded in comparison with the piston 3 shown in FIG. 4-1 and the piston 103 shown in FIG. 4-2, thus it may be reduced in the production yield, but the piston 203 has an advantage that change in the outer diameter of the piston can be comparatively freely designed, and contact area and contact angle between the outer periphery of the piston and the inner periphery of the barrel main body can be easily changed. In addition, the piston in which the hollow space is formed is preferable in terms of flexibility of the piston being adjustable by changing the size and shape of the hollow space.

In the medical syringe according to the present invention, as the medical syringe 1 shown in FIG. 1, it is preferable that the piston 3 and the plunger rod 4 are formed together by the integral molding in which the same resin material is used. If the above-mentioned structure is adopted, the medical syringe can be simple in structure and the substantial number of components can be reduced, thus the medical syringe can be manufactured at low cost.

However, in the present invention, it is not indispensable that the piston and the plunger rod are formed together by the integral molding in which the same resin material is used. For example, it can be also adopted that the piston and the plunger rod are individually molded, and then the components are assembled and integrated with each other. In addition, if a molding method such as a two-color molding and an insert molding is used, even if the piston and the plunger rod are respectively comprised of different resin materials, both the components can be integrally molded.

[1-3] Plunger Rod

As the medical syringe 1 shown in FIG. 1, the medical syringe according to the present invention includes the plunger rod 4 formed in a projecting manner at the end of the piston 3 in the shape of a rod having a diameter smaller than the piston 3. In addition, the plunger rod is held at the center of the barrel main body 21 in a state of being inserted into the rod insertion part of the plunger rod holder 5. Concrete value of the outer diameter of the plunger rod is not particularly limited, but it is preferable that the value falls within the range of 1.0 to 3.3 mm.

Figure 5:
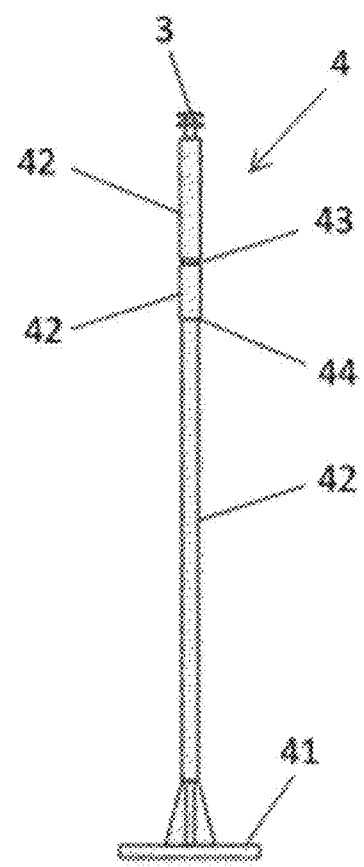
FIG. 5 is a side view schematically showing a plunger rod of the medical syringe shown in FIG. 1.

FIG. 5 is a side view schematically showing the plunger rod of the medical syringe shown in FIG. 1. As shown in FIG. 5, it is preferable that the medical syringe according to the present invention is configured such that the plunger rod 4 is integrally molded with the piston 3. However, the medical syringe according to the present invention can be also configured such that the piston is fitted into the tip of the plunger rod and the piston is screwed with the tip of the plunger rod.

As shown in FIG. 5, it is preferable that the medical syringe according to the present invention is configured such that the plunger rod 4 has an operation flange 41 at the end side thereof. The operation flange 41 is formed to have a larger area than a rod portion 42 and to have a structure that is easily caught by fingers, so that the operation flange 41 allows the plunger rod 4 to be easily operable to go forward or go backward. The shape of the operation flange is not particularly limited, but for example, a circular flat-plate shape and a quadrangular flat-plate shape can be used. In terms of ease of the operability, it is preferable that the operation flange is formed to have a circular flat-plate shape of approximately 1 to 5 cm in outer diameter.

As shown in FIG. 5, it is preferable that the medical syringe according to the present invention is configured such that the plunger rod 4 has a recessed groove 43 formed to temporarily fix the plunger rod 4 in a state of the piston 3 being located in the large inner diameter part of the barrel main body.

Figures 1, 7:
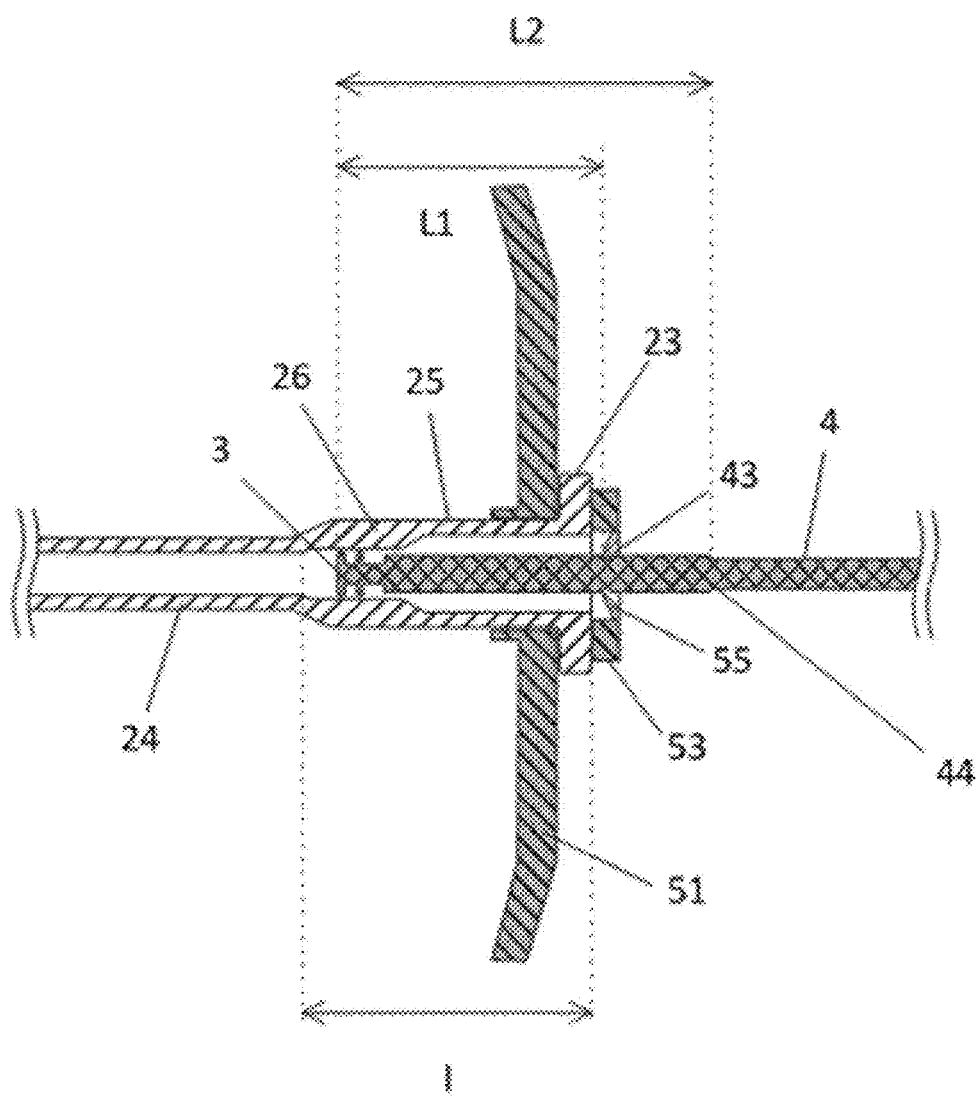
Figures 2, 7:
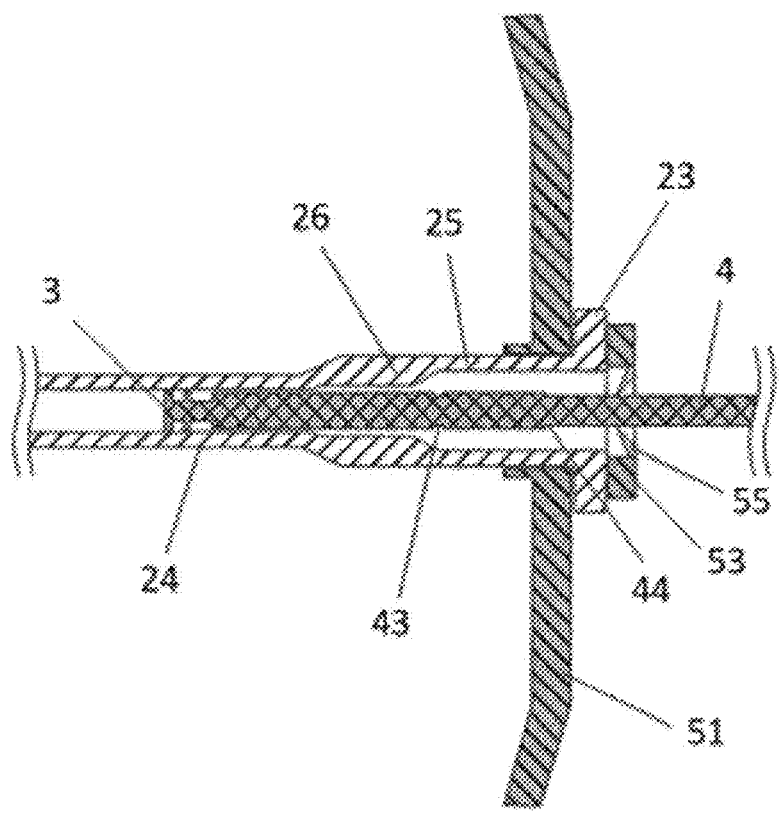
Figures 3, 7:
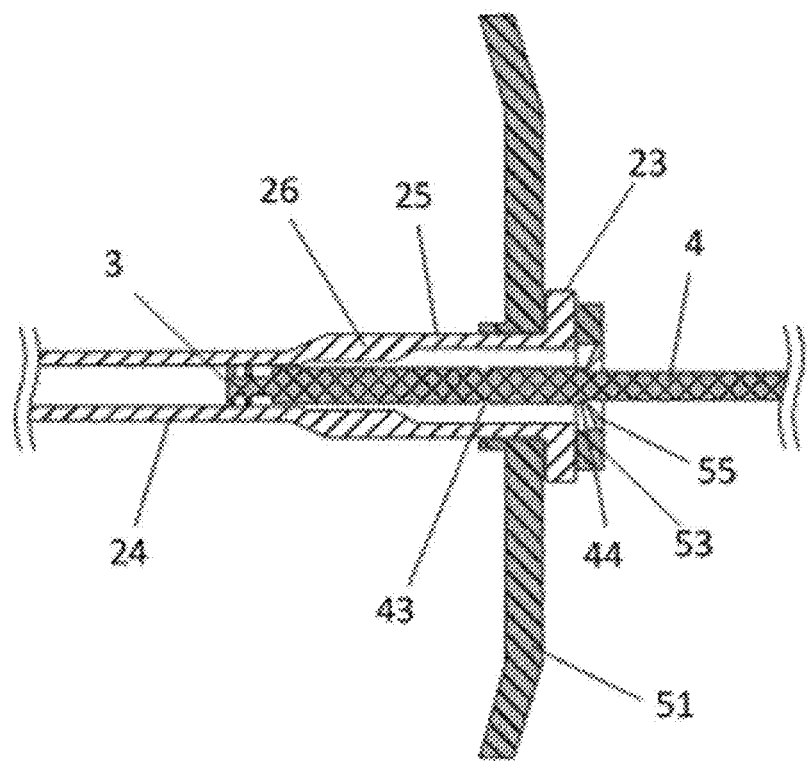

FIG. 7-1 is a conceptual view schematically showing a positional relationship between the respective components of the medical syringe shown in FIG. 1 in a state before use. As shown in FIG. 7-1, it is preferable that the medical syringe according to the present invention is configured such that the recessed groove 43 is formed at a position that the length L1 from the recessed groove 43 to the tip of the piston 3 is shorter than the length 1 of the large inner diameter part 25 of the barrel main body. This structure makes it possible to allow the piston 3 to locate in the large inner diameter part 25 of the barrel main body, when the recessed groove 43 is engaged with an inner edge portion (the tip of flexible boards 55) of the rod insertion part in the plunger rod holder. Consequently, a case that the piston 3 is unintentionally inserted into the small inner diameter part 24 of the barrel main body and is brought into contact with the inner periphery of the small inner diameter part 24 by pressurizing so as to cause the creep deformation can be effectively prevented.

The medical syringe according to the present invention can be also configured such that the recessed groove (not shown) is formed by disposing a pair of front and rear projecting portions in the outer periphery side of the plunger rod so as to enlarge the outer diameter of the plunger rod than those of the other parts. However, as shown in FIG. 5, it is preferable that the recessed groove 43 of the plunger rod 4 is formed by reducing the outer diameter of the plunger rod 4 (more particularly the outer diameter of the rod portion 42) than those of the other parts. The structure shown in FIG. 5 is more preferable than that formed by disposing a pair of projecting portions in terms of simplicity of structure and the ease of manufacture. The width and depth of the recessed groove 43 are not particularly limited, but it is preferable that the recessed groove 43 is formed such that the inner edge portion of the rod insertion part in the plunger rod holder can be surely engaged with the recessed groove 43. Particularly, it is preferable that the width falls within the range of 0.3 to 3.0 mm and the depth falls within the range of 0.1 to 1.0 mm.

As shown in FIG. 5, it is preferable that the medical syringe according to the present invention is configured such that the plunger rod 4 has a step part 44 formed not to allow the piston inserted into the small inner diameter part of the barrel main body to move backward to the large inner diameter part of the barrel main body. In addition, as shown in FIG. 7-1, it is preferable that the medical syringe according to the present invention is configured such that the step part 44 is formed at a position that the length L2 from the step part 44 to the tip of the piston 3 is longer than the length 1 of the large inner diameter part 25 of the barrel main body.

FIG. 7-2 is a conceptual view schematically showing a positional relationship between the respective components of the medical syringe shown in FIG. 1 in a state of use and FIG. 7-3 is a conceptual view schematically showing a positional relationship between the respective components in a state of the plunger rod of the medical syringe shown in FIG. 1 being pulled out at a maximum. As shown in FIG. 7-2, when the medical solution is filled in the medical syringe, the plunger rod 4 and the piston 3 are once pushed into the small inner diameter part 24 of the barrel main body and then the plunger rod 4 is pulled out, thereby the small inner diameter part 24 of the barrel main body is filled with the medical solution. As shown in FIG. 7-3, if the step part 44 is formed, when the step part 44 is engaged with the inner edge portion (the tip of flexible boards 55) of the rod insertion part in the plunger rod holder, the piston 3 can be located in the small inner diameter part 24 of the barrel main body. Namely, an accident that the plunger rod is excessively pulled out, thereby the piston is withdrawn from the small inner diameter part can be prevented.

As shown in FIG. 5, it is preferable that the medical syringe according to the present invention is configured such that the step part 44 of the plunger rod 4 is formed by reducing the outer diameter of the end side of the plunger rod 4 than that of the tip side thereof. The height of the step part 44 is not particularly limited, but it is preferable that the step part 44 is formed such that the inner edge portion of the rod insertion part in the plunger rod holder can be surely engaged with the step part 44. Particularly, it is preferable that the height falls within the range of 0.1 to 1.0 mm.

[1-4] Plunger Rod Holder

As the medical syringe 1 shown in FIG. 1, the medical syringe according to the present invention is configured to include a plunger rod holder 5 having a rod insertion part into which the plunger rod 4 can be inserted. In addition, the plunger rod holder 5 is mounted on the end of the barrel main body 21 so as to locate the rod insertion part at the center of the barrel main body 21. By the plunger rod holder, the plunger rod can be located at the center of the barrel main body.

In the medical syringe according to the present invention, the structure of the rod insertion part is not particularly limited, but it is preferable that the engagement structure of the recessed groove and the inner edge portion of the rod insertion part in the plunger rod holder is configured to permit only the movement in the insertion direction of the plunger rod and to inhibit the movement in the extraction direction of the plunger rod.

FIG. 6 is a perspective view schematically showing the plunger rod holder of the medical syringe shown in FIG. 1. As shown in FIG. 6, it is preferable that the medical syringe according to the present invention is configured such that the rod insertion part 54 of the plunger rod holder 5 includes a plurality of flexible boards 55 formed in a protruding manner in the inner edge portion side of the plunger rod holder 5 in a state of being slightly inclined in the insertion direction of the plunger rod. In the plunger rod holder 5 shown in FIG. 6, the flexible boards 55 are arranged in the inner edge of a flange fixing part 53 having a substantially "O" shape.

In the plunger rod holder 5 shown in FIG. 6, four flexible boards 55 are formed in a protruding manner at the inner edge side of the plunger rod holder 5 in a state of being slightly inclined with an angle of 45 degrees relative to the insertion direction of the plunger rod 4. In this structure, if the plunger rod 4 is tried to go backward in the extraction direction, the edge portion of the flexible boards 55 is engaged with the recessed groove of the plunger rod, so as to prevent the plunger rod from moving in the extraction direction. On the other hand, if the plunger rod 4 is tried to go forward in the insertion direction, the plunger rod is prevented to some extent from moving in the insertion direction by deflection elasticity of the flexible boards 55. However, the flexible boards 55 are formed to be slightly inclined in the insertion direction of the plunger rod, if a force that exceeds the deflection elasticity is applied thereto, the edge portion of the flexible boards 55 climbs over the recessed groove of the plunger rod so that the engagement between both components are released. Consequently, only the movement in the insertion direction of the plunger rod is permitted.

In the medical syringe according to the present invention, it is preferable that the rod insertion part of the plunger rod holder includes a plurality of flexible pins (not shown) formed in a protruding manner at the inner edge of the plunger rod holder in a state of being slightly inclined in the insertion direction of the plunger rod holder. Namely, instead of the flexible boards 55 as shown in FIG. 6, even if the structure that flexible pins (rod-like members) are formed in a protruding manner is adopted, the same effect can be obtained. It is preferable that the thickness of the flexible boards and the outer diameter of the flexible pins are formed so as to be surely engaged with the inner edge portion of the rod insertion part in the plunger rod holder. Concretely, it is preferable that the thickness of the flexible boards falls within the range of 0.5 to 2.0 mm and the outer diameter of the flexible pins falls within the range of 0.5 to 2.0 mm.

In the medical syringe according to the present invention, the structure for mounting the plunger rod holder in the end portion of the barrel main body is not particularly limited. For example, as the plunger rod holder 5 shown in FIG. 6, a structure that includes a barrel main body gripper 52 formed to have a shape that a flat plate is curved so as to be a substantially "C" shape, a flange fixing part 53 formed to be a flat plate having a substantially "O" shape and a connecting part 56 formed to have a shape that a flat plate is curved so as to be a substantially "C" shape and to connect the barrel main body gripper 52 to the flange fixing part 53 is preferably used. The barrel main body gripper 52 and the flange fixing part 53 are connected to each other with the connecting part 56 so as to form a void space corresponding to the thickness of the flange of the barrel main body. Consequently, the flange of the barrel main body is sandwiched between the barrel main body gripper 52 and the flange fixing part 53 and the barrel main body is gripped from the outer periphery surface side by the barrel main body gripper, thereby the plunger rod holder 5 shown in FIG. 6 can be mounted in the end portion of the barrel main body 21.

As shown in FIG. 6, in the medical syringe according to the present invention, it is preferable that plunger rod holder 5 has a finger catching part 51 formed in the end portion of the barrel main body gripper 52. The finger catching part is a component that allows the plunger rod to easily operable to go forward or go backward, similarly to the flange of the barrel main body. The finger catching part 51 shown in FIG. 6 has a two-blade shape that projects in the right and left side of the barrel main body gripper 52. In order to enhance operability of the medical syringe, similarly to the flange of the barrel main body, it is preferable that the projecting length thereof is set to a length that one side length is about 2 cm (at least not less than 1.5 cm) so as to be caught by adult fingers.

However, the shape of the finger catching part is not particularly limited to the two-blade shape as shown in FIG. 6. Similarly to the flange of the barrel main body, it can be also formed in a circular ring shape (not shown) that has an outer diameter of approximately 1.5 to 3 times the outer diameter of the barrel main body (the large inner diameter part). In addition, a position in which the finger catching part is arranged is not particularly limited to the end portion of the barrel main body gripper, but it can be arranged in an arbitrary position. For example, in the plunger rod holder 5 having a structure shown in FIG. 6, the finger catching part can be arranged in the tip of the barrel main body grippe 52 or in the flange fixing part 53 (not shown).

[1-5] Usage

Usage of the medical syringe according to the present invention will be explained by using FIGS. 7-1 to 7-3.

As shown in FIG. 7-1, in a state before use, the medical syringe according to the present invention is configured such that the flexible boards 55 formed in the rod insertion part of the plunger rod holder in a protruding manner are engaged with the recessed groove 43 of the plunger rod, and the piston 3 is fixed so as to be located in the large inner diameter part 25 of the barrel main body. In addition, the piston 3 is held in ribs 26 formed in the large inner diameter part 25 of the barrel main body in a state of being freely fitted thereto.

As shown in FIG. 7-2, the medical syringe according to the present invention is configured such that the piston 3 is pushed into the small inner diameter part 24 of the barrel main body, thereby the circular part of the piston 3 is brought into contact with the inner surface of the small inner diameter part 24 by pressurizing so that the medical solution can be sucked and injected. In this situation, the flexible boards 55 are not engaged with the recessed groove 43. Consequently, the piston 3 can be freely slid in the small inner diameter part 24 of the barrel main body.

Furthermore, as shown in FIG. 7-3, in a state of use or in a state after use, the medical syringe according to the present invention is configured such that even if the plunger rod 4 is tried to be pulled out in the end side thereof, the flexible boards 55 of the plunger rod holder is engaged with the step part 44 of the plunger rod 4, thereby the piston 3 does not go backward to the large inner diameter part 25 of the barrel main body. This structure makes it possible to prevent the medical solution from leaking from the end side of the medical syringe and to prevent air from being mixed into the medical solution from the large inner diameter part of the barrel main body.

As shown in FIGS. 7-1 to 7-3, the medical syringe 1 shown in FIG. 1 is configured such that the flexible boards 55 of the plunger rod holder can be engaged with both the recessed groove 43 and the step part 44 of the plunger rod 4, thus preferably, the position and movement of the plunger rod 4 can be precisely controlled even though the structure thereof is simple.

EXAMPLES

Example 1

As Example 1, the medical syringe 1 having a structure shown in FIG. 1 was manufactured.

[1] Syringe Barrel

By using a cycloolefin polymer (COP) that is a thermoplastic resin manufactured by Daikyo Seiko, Ltd. and sold by the trade name of "Daikyo Resin CZ" as a raw material, the syringe barrel 2 of a cylindrical shape having different diameters shown in FIG. 1 was molded. The syringe barrel 2 was formed to have an entire length of approximately 80 mm, and the nozzle 22 thereof was formed to have a length of 10 mm. The small inner diameter part 24 of the barrel main body 21 was formed to have a length of approximately 50 mm, an outer diameter of approximately 5 mm and an inner diameter of approximately 2.5 mm. The small inner diameter part 24 in which the medical solution is to be filled was formed to have a volume of approximately 0.2 mL. The large inner diameter part 25 of the barrel main body 21 was formed to have a length of approximately 20 mm, an outer diameter of approximately 7 mm and an inner diameter of approximately 4.8 mm.

Four ribs 26 were formed to respectively have a length of approximately 5 mm and a height of approximately 1 mm at intervals of 90 degrees of the center angle of the syringe barrel 2. A diameter of an inscribed circle inscribed in the tips of the four ribs 26 was approximately 2.8 mm. The flange 23 was formed in the end portion of the barrel main body 21. The flange 23 was formed in a circular ring shape that has an outer diameter of approximately 12 mm and formed to have a thickness of 1.5 mm.

[2] Piston, Plunger Rod

By using polypropylene that is a thermoplastic resin manufactured by Prime Polymer Co., Ltd. and sold by the trade name of "Prime Polypro" as a raw material, the plunger rod 4 having a structure shown in FIG. 5 was molded. The plunger rod 4 was formed such that an entire length was approximately 80 mm, an outer diameter of the rod-like part 42 was approximately 2.3 mm in both parts from the tip portion thereof to the recessed groove 43 and from the recessed groove 43 to the step part 44, and a depth of the recessed groove 43 and a height of the step part 44 were respectively 0.3 mm. The recessed groove 43 was formed to have a width of 0.5 mm. The rod-like part 42 was formed to have an outer diameter of approximately 2 mm in a part from the step part 44 to the end portion thereof. The operation flange 41 was formed in a circular ring shape that has an outer diameter of 15 mm and formed to have a thickness of 1.5 mm.

The piston 3 was integrally molded with the plunger rod 4 by using the above-mentioned polypropylene as a raw material. The piston 3 was formed to have a shape shown in FIG. 4-1. Namely, the piston 3 was formed to include the shaft portion 32 having a columnar shape and the brim portion 31 formed in the outer peripheral side of the shaft portion 32. The shaft portion 32 was formed in a columnar shape having an outer diameter of approximately 1.2 mm, and the brim portion 31 was formed in a plate-like shape having an outer diameter of approximately 2.6 mm and a thickness of approximately 0.2 mm. The shaft portion 32 was formed to have two brim portions 31 that were arranged at two places (one is the tip of the shaft portion 32 and another is a place located approximately 1 mm away from the tip toward the end side).

[3] Plunger Rod Holder

By using polypropylene manufactured by Prime Polymer Co., Ltd. and sold by the trade name of "Prime Polypro" as a raw material, the plunger rod holder 5 having a structure shown in FIG. 6 was molded. The plunger rod holder 5 was formed to have a structure that includes the barrel main body gripper 52 formed to have a shape that a flat plate is curved so as to be a substantially "C" shape, the flange fixing part 53 formed to be a flat plate having a substantially "O" shape and the connecting part 56 formed to have a shape that a flat plate is curved so as to be a substantially "C" shape and to connect the barrel main body gripper 52 to the flange fixing part 53.

The barrel main body gripper 52 was formed in a substantially "C" shape having an inner diameter of approximately 7 mm and an outer diameter of approximately 9.5 mm. Both ends of the substantially "C" shape were bent so as to be opened outward. The both ends were bent so as to form an angle of 70 degrees with each other.

The flange fixing part 53 was formed to be a flat plate of a substantially "O" shape having an outer diameter of approximately 10 mm, an inner diameter of approximately 5 mm and a thickness of approximately 1 mm, and in the center opening thereof, four flexible boards 55 having a length of approximately 1.5 mm and a thickness of approximately 1 mm were formed in a protruding manner. The flexible boards 55 were formed in a protruding manner in a state of being slightly inclined with an angle of 45 degrees relative to the insertion direction of the plunger rod. The tips of the four flexible boards 55 were not brought into contact with each other and were arranged so as to form a circular opening having an inner diameter of 2 mm (the rod insertion part 54). The barrel main body gripper 52 and the flange fixing part 53 were connected to each other by the connecting part 56 having a substantially "C" shape so as to form an air space of 1.5 mm between them.

The finger catching part 51 was formed to have a two-blade shape projecting in the right and left sides of the barrel main body 52. The finger catching part 51 was formed to have a width of approximately 12 mm, a thickness of approximately 1 mm and a projecting length of approximately 18 mm in one side.

[4] Medical Syringe

The syringe barrel, the piston, the plunger rod and the plunger rod holder that were molded as described above were assembled with each other, thereby a medical syringe of Example 1 was obtained.

Example 2

A medical syringe was manufactured similarly to Example 1 except that the shape of the piston was changed to that shown in FIG. 4-2. The piston 103 was configured such that a part of the shaft portion 132 sandwiched between two brim portions 131 was formed in a columnar shape having an outer diameter of approximately 1.8 mm.

Example 3

A medical syringe was manufactured similarly to Example 1 except that the shape of the piston was changed to a substantially barrel-like shape shown in FIG. 4-3. The piston 203 was formed in a substantially barrel-like shape configured to have an entire length of 3 mm, and a part having an outer diameter of approximately 2.6 mm (maximum value) located approximately 1 mm away from the tip toward the end side, the outer diameter being gradually reduced from the part to the tip and end of the piston. The tip and the end of the piston 203 were formed to have an outer diameter of approximately 2.3 mm, and the end of the piston 203 was formed to be connected to the tip of the plunger rod having an outer diameter of approximately 2.3 mm. In addition, an air space 233 was formed in a columnar shape having an inner diameter of approximately 1.9 mm and a length of approximately 3 mm within the piston 203 having the substantially barrel-like shape.

Examples 4 to 6

Medical syringes were manufactured similarly to Examples 1 to 3 except that a height of the ribs formed in the large inner diameter part of the barrel main body was adjusted, thereby a diameter of an inscribed circle inscribed in the tips of the four ribs was changed to approximately 2.6 mm. Example corresponding to Example 1 is referred to as Example 4, Example corresponding to Example 2 is referred to as Example 5 and Example corresponding to Example 3 is referred to as Example 6.

Comparative Examples 1 to 3

Medical syringes were manufactured similarly to Examples 1 to 3 except that the large inner diameter part was not formed in the barrel main body. Namely, the barrel main body was formed to have an outer diameter of approximately 5 mm, an inner diameter of approximately 2.5 mm and a length of approximately 70 mm so as to be configured to have only the small inner diameter part. Comparative Example corresponding to Example 1 is referred to as Comparative Example 1, Comparative Example corresponding to Example 2 is referred to as Comparative Example 2 and Comparative Example corresponding to Example 3 is referred to as Comparative Example 3.

[Sealing Properties Test]

The medical syringes of Example 1 to 6 were stored in a state of the piston being located in the large inner diameter part of the barrel main body at normal temperature in dark place for 3 days, 3 months, 6 months, and 1 year after the manufacture, and the medical syringes of Comparative Example 1 to 3 were stored in a state of the piston being located in the barrel main body corresponding to the small inner diameter part under the same conditions. After that, with regard to the respective medical syringes, the plunger rod was pushed into the syringe barrel at a maximum, a syringe needle of 31 G in diameter was mounted on the nozzle, the barrel main body was fixed in a state of the tip of the syringe needle being inserted into water poured into a beaker, and the plunger rod was fixed to a testing machine manufactured by Shimadzu Corporation and sold by the trade name of "Autograph" (model number "AG-5kNIS MS", load cell 100N) by using a fixing tool.

When the plunger rod was pulled out by approximately 45 mm from the above-mentioned state at the respective movement speeds of 100 mm/min and 200 mm/min, and approximately 0.2 mL of water was sucked into the medical syringe, existence or nonexistence of an air leak from the piston side was visually observed.

Similarly, when the water sucked as described above was injected at the respective movement speeds of 100 mm/min and 200 mm/min, existence or nonexistence of a water leak from the piston side was visually observed. The number of the test relating to the respective medical syringes was 10, and Tables 1, 2 show the number of the medical syringe in which the leak occurred.

TABLE 2

| Sealing property | Comparative Example 1 | | Comparative Example 2 | | Comparative Example 3 | |
|---|---|---|---|---|---|---|
| (Number per 10) | Suction | Injection | Suction | Injection | Suction | Injection |
| After 3 days | | | | | | |
| 100 (mm/min) | 1 | 0 | 0 | 0 | 0 | 0 |
| 200 (mm/min) | 4 | 1 | 0 | 0 | 0 | 0 |
| After 3 months | | | | | | |
| 100 (mm/min) | 4 | 2 | 2 | 0 | 1 | 0 |
| 200 (mm/min) | 7 | 5 | 4 | 2 | 2 | 0 |
| After 6 months | | | | | | |
| 100 (mm/min) | 10 | 8 | 9 | 8 | 5 | 2 |
| 200 (mm/min) | 10 | 10 | 10 | 10 | 8 | 4 |
| After 1 year | | | | | | |
| 100 (mm/min) | 10 | 9 | 10 | 9 | 7 | 6 |
| 200 (mm/min) | 10 | 10 | 10 | 10 | 9 | 9 |

As is clear from the results shown in Tables 1, 2, the medical syringes of Examples 1 to 6 exhibited good results such that an air leak at the time of suction and a water leak at the time of injection did not occur at all even after 1 year from the manufacture. On the other hand, in the syringes of Comparative Examples 1 to 3, the air leak at the time of suction and the water leak at the time of injection occurred. Namely, the medical syringes of Examples 1 to 6 were capable of effectively preventing an occurrence of creep deformation in the piston.

[Sliding Friction Test]

In the above-mentioned sealing properties test, the maximum value (N) of sliding friction value of the piston was measured by the testing machine "Autograph" at the time of suction of water. Tables 3, 4 show average values of the maximum values in the tests carried out ten times. Normally, the sliding friction value is used as an index of the ease of movement of the piston. However, it is considered that if the piston is firmly fixed to an inner wall of the syringe barrel (barrel main body), the sliding friction value is increased, and if the piston is creep-deformed, the sliding friction value is decreased. Namely, the sliding friction value can be also used as an index of the firm fixing between the piston and the syringe barrel, and the creep deformation.

TABLE 1

| Sealing property | Example 1 | | Example 2 | | Example 3 | | Example 4 | | Example 5 | | Example 6 | |
|---|---|---|---|---|---|---|---|---|---|---|---|---|
| (Number per 10) | Suction | Injection | Suction | Injection | Suction | Injection | Suction | Injection | Suction | Injection | Suction | Injection |
| After 3 days | | | | | | | | | | | | |
| 100 (mm/min) | 0 | 0 | 0 | 0 | 0 | 0 | 0 | 0 | 0 | 0 | 0 | 0 |
| 200 (mm/min) | 0 | 0 | 0 | 0 | 0 | 0 | 0 | 0 | 0 | 0 | 0 | 0 |
| After 3 months | | | | | | | | | | | | |
| 100 (mm/min) | 0 | 0 | 0 | 0 | 0 | 0 | 0 | 0 | 0 | 0 | 0 | 0 |
| 200 (mm/min) | 0 | 0 | 0 | 0 | 0 | 0 | 0 | 0 | 0 | 0 | 0 | 0 |
| After 6 months | | | | | | | | | | | | |
| 100 (mm/min) | 0 | 0 | 0 | 0 | 0 | 0 | 0 | 0 | 0 | 0 | 0 | 0 |
| 200 (mm/min) | 0 | 0 | 0 | 0 | 0 | 0 | 0 | 0 | 0 | 0 | 0 | 0 |
| After 1 year | | | | | | | | | | | | |
| 100 (mm/min) | 0 | 0 | 0 | 0 | 0 | 0 | 0 | 0 | 0 | 0 | 0 | 0 |
| 200 (mm/min) | 0 | 0 | 0 | 0 | 0 | 0 | 0 | 0 | 0 | 0 | 0 | 0 |

TABLE 3

| Sliding friction value (N) | Example 1 Suction | Example 2 Suction | Example 3 Suction | Example 4 Suction | Example 5 Suction | Example 6 Suction |
|---|---|---|---|---|---|---|
| After 3 days | | | | | | |
| 100 (mm/min) | 1.43 | 1.56 | 2.84 | 1.38 | 1.51 | 2.8 |
| 200 (mm/min) | 1.66 | 1.83 | 3.23 | 1.66 | 1.92 | 3.21 |
| After 3 months | | | | | | |
| 100 (mm/min) | 1.42 | 1.58 | 2.74 | 1.32 | 1.55 | 2.76 |
| 200 (mm/min) | 1.64 | 1.78 | 3.32 | 1.64 | 1.83 | 3.16 |
| After 6 months | | | | | | |
| 100 (mm/min) | 1.41 | 1.62 | 2.96 | 1.33 | 1.53 | 2.92 |
| 200 (mm/min) | 1.66 | 1.86 | 3.43 | 1.60 | 1.80 | 3.23 |
| After 1 year | | | | | | |
| 100 (mm/min) | 1.44 | 1.54 | 2.86 | 1.32 | 1.47 | 2.72 |
| 200 (mm/min) | 1.62 | 1.84 | 3.33 | 1.60 | 1.78 | 3.20 |

TABLE 4

| Sliding friction value (N) | Comparative Example 1 Suction | Comparative Example 2 Suction | Comparative Example 3 Suction |
|---|---|---|---|
| After 3 days | | | |
| 100 (mm/min) | 1.33 | 1.36 | 2.46 |
| 200 (mm/min) | 1.52 | 1.53 | 2.73 |
| After 3 months | | | |
| 100 (mm/min) | 1.13 | 1.14 | 2.13 |
| 200 (mm/min) | 1.28 | 1.33 | 2.42 |
| After 6 months | | | |
| 100 (mm/min) | 1.06 | 1.12 | 1.91 |
| 200 (mm/min) | 1.22 | 1.27 | 2.21 |
| After 1 year | | | |
| 100 (mm/min) | 1.03 | 1.05 | 1.86 |
| 200 (mm/min) | 1.18 | 1.22 | 2.11 |

As is clear from the results shown in Tables 3, 4, the medical syringes of Examples 1 to 6 exhibited good results such that the sliding friction value was almost not changed even after 1 year from the manufacture. On the other hand, in the syringes of Comparative Examples 1 to 3, the sliding friction value was slightly reduced with time. Namely, the medical syringes of Examples 1 to 6 were capable of effectively preventing an occurrence of creep deformation in the piston. Further, in any medical syringe of Examples 1 to 6 and Comparative Examples 1 to 3, the sliding friction value was not increased and the fixing of the piston was not observed. In addition, any medical syringe described above was configured such that the piston was good in the ease of movement, thus it was included in a usable range.

Although the invention has been described with respect to the specific embodiments for complete and clear disclosure, the appended claims are not to be thus limited but are to be construed as embodying all modifications and alternative constructions that may occur to one skilled in the art which fairly fall within the basic teaching herein set forth.

INDUSTRIAL APPLICABILITY

The medical syringe according to the present invention can be preferably used as a filled-in use type syringe in which the medical solution is filled at the time of use, in particular, as a medical syringe having small volume such as a microliter syringe.

CROSS-REFERENCE TO RELATED APPLICATION

This application claims the priority of Japanese Patent Application 2012-288551 filed Dec. 28, 2012, which is incorporated herein by reference.

REFERENCE SIGNS LIST 1, 100: syringe
2: syringe barrel
21: barrel main body
22: nozzle
23: flange
24: small inner diameter part
25, 125: large inner diameter part
26: rib
27: Luer lock
3, 103, 203: piston
31, 131: brim portion
32, 132: shaft portion
233: hollow space
4: plunger rod
41: operation flange
42: rod portion
43: recessed groove
44: step part
5: plunger rod holder
51: finger catching part
52: barrel main body gripper
53: flange fixing part
54: rod insertion part
55: flexible board
56: connecting part

The invention claimed is:

1. A filled-in use type medical syringe, comprising:
a syringe barrel having a barrel main body formed in a substantially cylindrical shape, a nozzle formed at the tip of the barrel main body and a flange formed at the end of the barrel main body;
a piston having a circular part which has an outer diameter that can be inserted into an interior space of the barrel main body; and
a plunger rod formed at a first end of the piston in a protruding manner in the shape of a rod having a diameter smaller than the outer diameter of the circular part of the piston, and
a plunger rod holder having a rod insertion part into which the plunger rod can be inserted,
wherein the barrel main body is formed to have a small inner diameter part on a tip side thereof, and have a large inner diameter part that has a larger inner diameter than the small inner diameter part on an end side thereof, the large inner diameter part having a plurality of integral ribs that project toward a center of the large diameter part and extend longitudinally in a direction parallel to the axis direction of the syringe barrel, the ribs being configured so that the piston can be held in the plurality of ribs in a freely-fitted state,
the circular part of the piston is comprised of an elastic material and has an outer diameter larger than the inner diameter of the small inner diameter part of the barrel main body so that an outer periphery of the circular part can be pressed by an inner peripheral surface of the small inner diameter part while sliding along the small inner diameter part, the piston being configured to establish sealing engagement with the inner peripheral surface of the small inner diameter part for suction and injection of medical solution into and from the barrel main body, and the circular part of the piston has an outer diameter smaller than the inner diameter of the larger inner diameter part of the barrel main body, the plunger rod holder is mounted on an outer surface of the end of the barrel main body so that the rod insertion part is located at the center of the barrel main body, the plunger rod is held at the center of the barrel main body in a state of being inserted into the rod insertion part of the plunger rod holder, and the larger inner diameter part remains free from a medical solution held by the syringe when the syringe is filled for use.

2. The medical syringe according to claim 1, wherein the piston comprises a shaft portion and a brim portion as the circular part formed in an outer peripheral side of the shaft portion, the brim portion is comprised of a resin and the brim portion of the piston has an outer diameter smaller than the inner diameter of the larger inner diameter part of the barrel main body.

3. The medical syringe according to claim 1, wherein the plunger rod has a recessed groove formed to temporarily fix the plunger rod in a state of the piston being located in the large inner diameter part of the barrel main body, the recessed groove is formed by reducing an outer diameter of the plunger rod relative to that of parts adjacent to the recessed groove, the recessed groove is formed at a position that a length from the recessed groove to a second end of the piston that is closer to the tip side of the barrel main body than the first end of the piston is shorter than a length of the large inner diameter part of the barrel main body, and when the recessed groove is engaged with an inner edge portion of the rod insertion part in the plunger rod holder, the piston is located in the large inner diameter part of the barrel main body.

4. The medical syringe according to claim 1, wherein the plunger rod has a recessed groove configured to temporarily fix the plunger rod in a state that the piston is located in the large inner diameter part of the barrel main body, the recessed groove is formed by disposing a pair of front and rear projecting portions in an outer periphery side of the plunger rod so as to enlarge an outer diameter of the plunger rod relative to that of parts between the projecting portions, the recessed groove is formed at a position that a length from the recessed groove to a second end of the piston that is closer to the tip side of the barrel main body than a first end of the piston is shorter than a length of the large inner diameter part of the barrel main body, and when the recessed groove is engaged with an inner edge portion of the rod insertion part in the plunger rod holder, the piston is located in the large inner diameter part of the barrel main body.

5. The medical syringe according to claim 3, wherein the engagement structure of the recessed groove and the inner edge portion is configured to permit only movement in an insertion direction of the plunger rod and to inhibit movement in an extraction direction of the plunger rod.

6. The medical syringe according to claim 5, wherein the rod insertion part of the plunger rod holder comprises a plurality of flexible boards formed in a protruding manner in an inner edge portion side of the plunger rod holder in a state of being slightly inclined in the insertion direction of the plunger rod.

7. The medical syringe according to claim 5, wherein the rod insertion part of the plunger rod holder comprises a plurality of flexible pins formed in a protruding manner in an inner edge portion side of the plunger rod holder in a state of being slightly inclined in the insertion direction of the plunger rod.

8. The medical syringe according to claim 1, wherein the plunger rod has a step part formed so as not to allow the piston inserted into the small inner diameter part of the barrel main body to move to the large inner diameter part of the barrel main body, wherein the step part is formed by a reduced outer diameter of a first portion of the plunger rod distal to the piston relative to a second portion of the plunger rod close to the piston, the step part is formed at a position such that a length from the step part to a second end of the piston that is closer to the tip side of the barrel main body than a first end of the piston is longer than a length of the large inner diameter part of the barrel main body, and when the step part is engaged with an inner edge portion of the rod insertion part in the plunger rod holder, the piston is located in the small inner diameter part of the barrel main body.

9. The medical syringe according to claim 1, wherein the piston is comprised of a thermoplastic elastomer or a thermoplastic resin.

10. The medical syringe according to claim 1, wherein the small inner diameter part and the large inner diameter part each have circular cylindrical cross sections.

11. The medical syringe according to claim 1, wherein the outer periphery of the circular part comprises a cylindrical surface, and the cylindrical surface can be pressed by the inner peripheral surface of the small inner diameter part while sliding along the small inner diameter part.

12. The medical syringe according to claim 1, wherein a portion of the piston establishing the sealing engagement is not subjected to a compressing force when the piston is positioned in the large inner diameter part of the main barrel body.

13. A filled-in use type medical syringe, comprising:

a syringe barrel having a barrel main body formed in a substantially cylindrical shape, a nozzle formed at the tip of the barrel main body and a flange formed at the end of the barrel main body;

a piston having a circular part which has an outer diameter that can be inserted into an interior space of the barrel main body; and a plunger rod formed at a first end of the piston in a protruding manner in the shape of a rod having a diameter smaller than the outer diameter of the circular part of the piston, and a plunger rod holder having a rod insertion part into which the plunger rod can be inserted, wherein the barrel main body is formed to have a small inner diameter part on a tip side thereof, and have a large inner diameter part that has a larger inner diameter than the small inner diameter part on an end side thereof, the large inner diameter part having a plurality of integral ribs that project toward a center of the large diameter part and extend longitudinally in a direction parallel to the axis direction of the syringe barrel so that the piston can be held in the plurality of ribs in a freely-fitted state, and the piston is kept in the small inner diameter part of the barrel main body so as not move to the large inner diameter part of the barrel main body when the syringe is in use, the circular part of the piston is comprised of an elastic material and has an outer diameter larger than the inner diameter of the small inner diameter part of the barrel main body so that an outer periphery of the circular part can be pressed by an inner peripheral surface of the small inner diameter part while sliding along the small inner diameter part, the piston being configured to establish sealing engagement with the inner peripheral surface of the small inner diameter part for suction and injection of medical solution into and from the barrel main body, and the circular part of the piston has an outer diameter smaller than the inner diameter of the larger inner diameter part of the barrel main body, wherein the piston is held in the large inner diameter part of the barrel main body in a state of being freely fitted thereto before the syringe is in use, and the piston remains in the small inner diameter part when the syringe is in use, the plunger rod holder is mounted on an outer surface of the end of the barrel main body so that the rod insertion part is located at the center of the barrel main body, the plunger rod is held at the center of the barrel main body in a state of being inserted into the rod insertion part of the plunger rod holder, and the larger inner diameter part remains free from a medical solution held by the syringe when the syringe is filled for use.

\* \* \* \* \*